US009687651B2

(12) United States Patent
Karunasiri

(10) Patent No.: US 9,687,651 B2
(45) Date of Patent: Jun. 27, 2017

(54) SYSTEMS AND METHODS FOR MEASURING ELECTRODE IMPEDANCE DURING A NORMAL OPERATION OF A COCHLEAR IMPLANT SYSTEM

(71) Applicant: ADVANCED BIONICS AG, Staefa (CH)

(72) Inventor: R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,023

(22) PCT Filed: Oct. 9, 2013

(86) PCT No.: PCT/US2013/064100
§ 371 (c)(1),
(2) Date: Mar. 22, 2016

(87) PCT Pub. No.: WO2015/053769
PCT Pub. Date: Apr. 16, 2015

(65) Prior Publication Data
US 2016/0235984 A1    Aug. 18, 2016

(51) Int. Cl.
*A61N 1/36* (2006.01)
*A61N 1/05* (2006.01)

(52) U.S. Cl.
CPC ....... *A61N 1/36032* (2013.01); *A61N 1/0541* (2013.01)

(58) Field of Classification Search
None
See application file for complete search history.

(56) References Cited

U.S. PATENT DOCUMENTS 5,674,264 A * 10/1997 Carter ................. H04R 25/505
                                                         607/57
7,031,773 B1    4/2006 Levine et al.
7,206,640 B1    4/2007 Overstreet
(Continued)

FOREIGN PATENT DOCUMENTS

EP         0338364 B1    7/1994

OTHER PUBLICATIONS

International Search Report and Written Opinion in International Application No. PCT/US13/064100, dated Feb. 19, 2014.

*Primary Examiner* — Brian T Gedeon
(74) *Attorney, Agent, or Firm* — ALG Intellectual Property, LLC

(57) ABSTRACT

An exemplary sound processor may include a stimulation management facility that 1) receives an audio signal presented to the patient during a normal operation of the cochlear implant system, and 2) directs a cochlear implant of the cochlear implant system to generate and apply an electrical stimulation pulse representative of the audio signal by way of an electrode included in a plurality of electrodes coupled to the cochlear implant. The sound processor may further include an impedance management facility that determines an impedance of the electrode by directing the cochlear implant to measure a voltage level associated with the electrode while the electrical stimulation pulse is being applied by way of the electrode. Corresponding systems and methods are also described.

20 Claims, 7 Drawing Sheets

(56) References Cited

U.S. PATENT DOCUMENTS

| | | | |
|---|---|---|---|
| 7,571,007 B2* | 8/2009 | Erickson | A61N 1/3787 607/61 |
| 8,265,766 B1* | 9/2012 | Kulkarni | A61N 1/36032 607/55 |
| 8,527,058 B2* | 9/2013 | Kulkarni | A61N 1/36032 607/32 |
| 8,751,006 B2* | 6/2014 | Saoji | A61N 1/36032 607/32 |
| 9,144,687 B2* | 9/2015 | Griffith | A61N 1/37252 |
| 2004/0094355 A1* | 5/2004 | Goorevich | A61N 1/37252 181/129 |
| 2012/0053656 A1 | 3/2012 | Chapa et al. | |
| 2012/0316454 A1 | 12/2012 | Carter | |
| 2013/0204154 A1* | 8/2013 | Loi | A61B 5/0478 600/544 |

* cited by examiner

SYSTEMS AND METHODS FOR MEASURING ELECTRODE IMPEDANCE DURING A NORMAL OPERATION OF A COCHLEAR IMPLANT SYSTEM

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

Each electrode implanted within the cochlea has a certain impedance associated therewith. The impedance is often used to determine one or more stimulation parameters during an initial fitting session to fit a cochlear implant system to a patient. However, the impedance of an electrode may change over time, thus resulting in decreased sound quality, distorted pitch, and/or system malfunction.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for measuring electrode impedance during a normal operation of a cochlear implant system are described herein. As will be described below, a sound processor included in a cochlear implant system associated with a patient may include a stimulation management facility that 1) receives an audio signal presented to the patient during a normal operation of the cochlear implant system, and 2) directs a cochlear implant of the cochlear implant system to generate and apply an electrical stimulation pulse representative of the audio signal by way of an electrode included in a plurality of electrodes coupled to the cochlear implant. The sound processor may also include an impedance management facility that determines an impedance of the electrode by directing the cochlear implant to measure a voltage level associated with the electrode while the electrical stimulation pulse is being applied by way of the electrode. The stimulation management facility may adjust one or more stimulation parameters associated with the cochlear implant system based on the determined impedance.

As used herein, a "normal operation" of the cochlear implant system refers to an operation of the cochlear implant system that occurs during a time period in which an electrical stimulation pulse, representative of an audio signal, is generated and applied by way of an electrode associated with a cochlear implant. In other words, the cochlear implant system is in a normal operation when it is being used to generate and apply electrical stimulation representative of an audio signal to a cochlear implant patient (as opposed to modes of operation in which the cochlear implant system is being fitted to the patient, starting up, and/or initializing). The audio signal may represent any sound presented to the patient during the time period. As will be described herein, the electrical stimulation pulse applied by way of the electrode to represent the audio signal may also be used to measure the impedance of the electrode. This is in contrast to conventional techniques that use a signal specifically generated (e.g., during an initialization and/or fitting procedure) to measure the impedance of the electrode (i.e., a signal that does not represent an audio signal presented to the patient).

The systems and methods described herein may advantageously allow for dynamic detection of an impedance of an electrode at normal stimulation levels and during a normal operation of the cochlear implant system. As a result, the systems and methods described herein may facilitate adjusting and/or optimizing stimulation parameters of a cochlear implant system on-the-fly to account for variations in impedance that occur in the electrode over time. Such adjustment and/or optimization may result in improved cochlear implant system performance. Other benefits of the systems and methods described herein will be made apparent herein.

Figure 1:
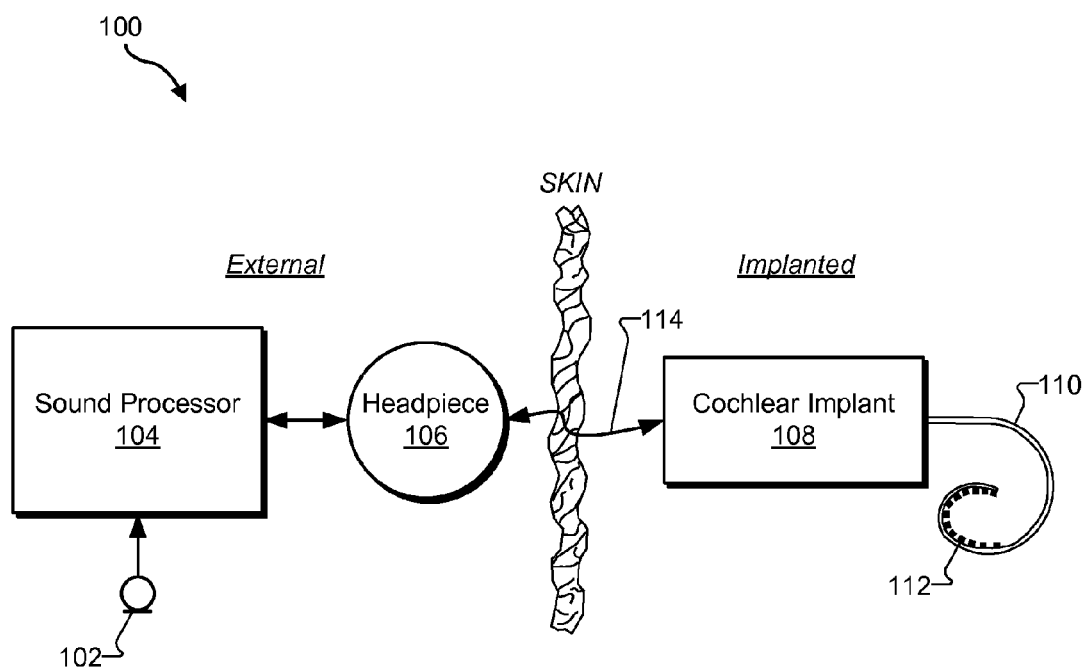
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112. For ease of explanation, the following description refers to one of the electrodes included in electrodes 112. It will be understood that the impedance for any and all of the electrodes included in electrodes 112 may be separately determined according to principles described herein.

Figure 2:
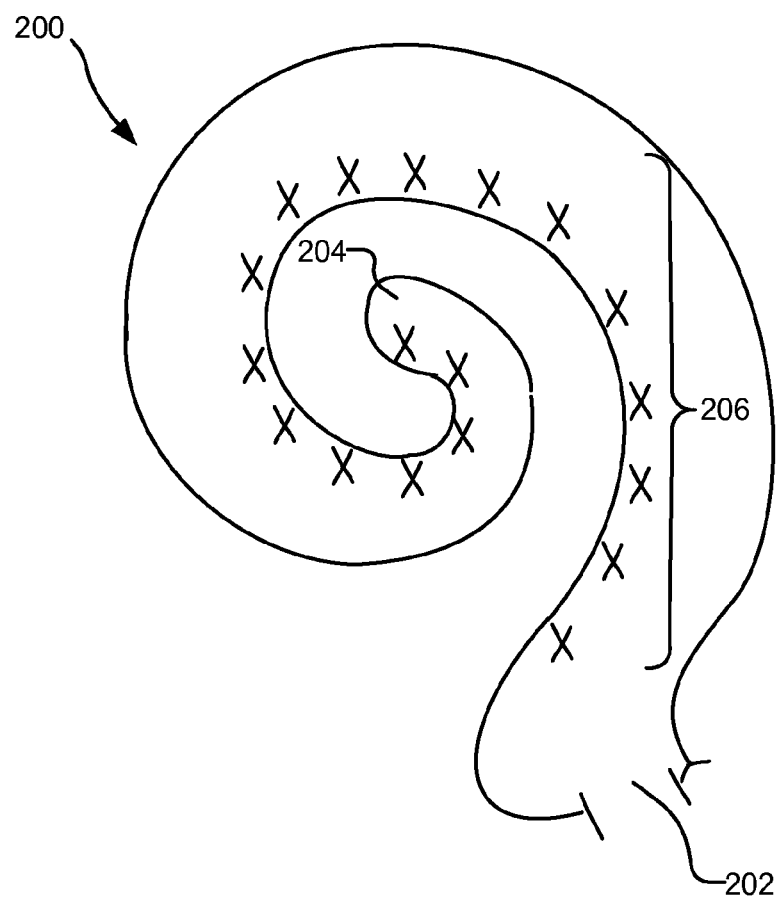
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
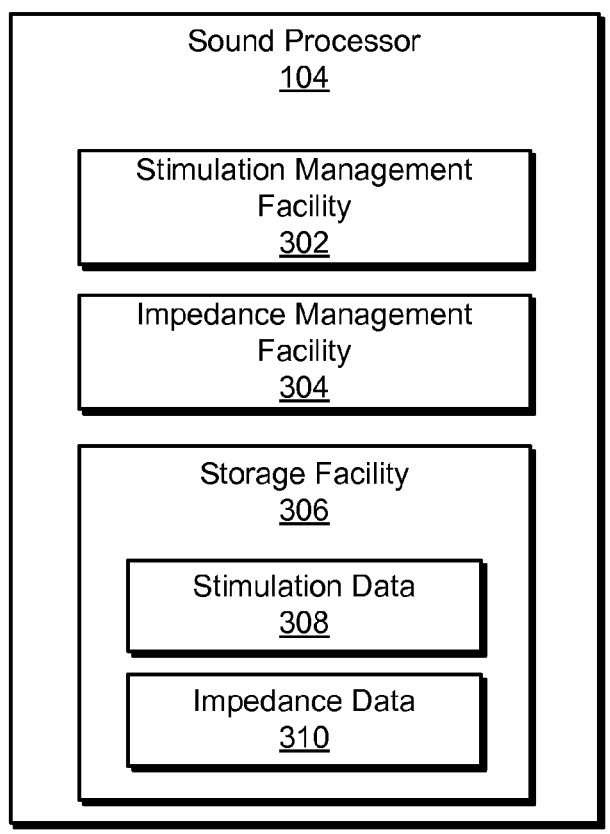
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a stimulation management facility 302, an impedance management facility 304, and a storage facility 306, which may be in communication with one another using any suitable communication technologies. Storage facility 306 may be configured to maintain stimulation data 308 generated and/or used by stimulation management facility 302, and impedance data 310 (e.g., data representative of one or more electrode impedances) measured by impedance management facility 304 and/or used by stimulation management facility 302. Storage facility 306 may maintain additional or alternative data as may serve a particular implementation. One or more of facilities 302-306 may include a computing device or processor configured to perform one or more of the functions described herein. Facilities 302-306 will now be described in more detail.

Stimulation management facility 302 may be configured to perform various stimulation management operations with respect to an audio signal presented to a cochlear implant patient (e.g., an audio signal detected by microphone 102, an audio signal input by way of an auxiliary audio input port, etc.). For example, stimulation management facility 302 may receive the audio signal presented to a cochlear implant patient during a normal operation of the cochlear implant system 100. Stimulation management facility 302 may then perform one or more pre-processing operations, spectral analysis operations, noise reduction operations, mapping operations, and/or any other types of signal processing operations with respect to the received audio signal as may serve a particular application.

Once the audio signal has been processed, stimulation management facility 302 may direct cochlear implant 108 to generate and apply an electrical stimulation pulse representative of the audio signal by way an electrode (e.g., one of electrodes 112) coupled to the cochlear implant 108. The electrical stimulation pulse may be generated and applied by cochlear implant 108 in any suitable manner.

As mentioned, an impedance may be associated with the electrode. The impedance may be dependent of the physiological properties of the tissue where the electrode is implanted, the composition of the electrode itself, and/or any other factor as may serve a particular application.

According to Ohm's law, the relationship between the voltage ("V") generated by a voltage source, the current ("I") applied to the electrode, and the impedance ("Z") of the electrode is $V=I*Z$. Thus, with a fixed maximum voltage, a change in impedance will cause an opposite change in the maximum current that may be applied to the electrode. For example, an increase in impedance would cause a decrease in maximum current, which in turn would cause a decrease in the total charge per phase applied to a stimulation site. This change in total charge applied to the stimulation site may have adverse effects on the loudness level or sound quality of an audio signal experienced by a patient.

A change in electrode impedance may be caused by many different factors. For example, changes in one or more physiological properties of tissue within the cochlea, aging, a change in body fat percentage, introduction of scar tissue, dehydration, and/or infection may lead to a change in electrode impedance. A change in electrode impedance may additionally or alternatively be caused by an electrode malfunction (e.g., an electrode may become shorted or open). A change in electrode impedance may be permanent in some instances (e.g., with aging) or temporary in others (e.g., during an infection). In addition, variations in electrode impedance may occur at different times during a day.

As mentioned, a change in electrode impedance may result in a degradation of sound quality experienced by a patient. For example, a change in electrode impedance may result in a change in loudness level and/or distort pitch.

Such sound quality degradation may adversely affect the ability of the patient to recognize speech, music, and/or other sounds. This can be especially devastating for pediatric cochlear implant patients because the change in sound quality or volume may go unnoticed for long periods of time. Hence, an undetected change in electrode impedance can potentially interfere with the overall speech and language development of pediatric patients. It will be recognized that cochlear implant patients of all ages may experience similar difficulties if a change in electrode impedance is not detected and accounted for. As will be discussed in more detail below, a change in impedance may be compensated for by adjusting one or more stimulation parameters governing an operation of cochlear implant 108. In some examples, the adjustment of stimulation parameters may be configured to maintain constant a total charge per phase applied to a stimulation site within the cochlea.

In view of the above, impedance management facility 304 may determine the impedance of the electrode while the electrical stimulation pulse is being applied by way of the electrode. In some examples, this may be done by directing cochlear implant 108 to measure a voltage level associated with the electrode while the electrical stimulation pulse is being applied by way of the electrode. The voltage level, together with the known current level of the electrical stimulation pulse, may then be used by impedance management facility 304 to determine the impedance of the electrode (e.g., by using Ohm's law to calculate the impedance).

Figure 4:
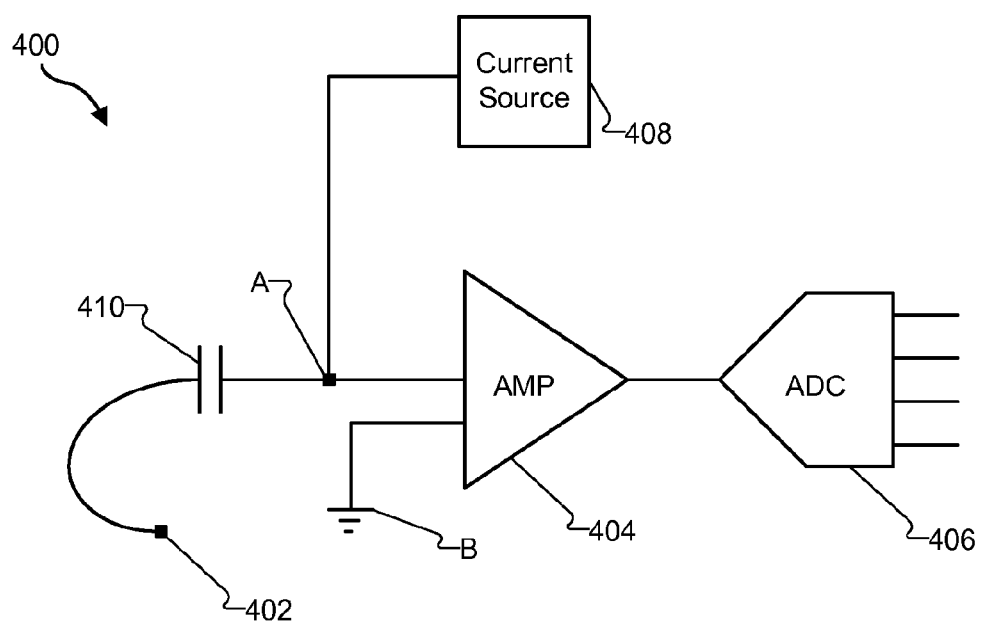
FIG. 4 illustrates an exemplary voltage measuring circuit according to the principles described herein.

To this end, cochlear implant 108 may include a voltage measuring circuit configured to measure the voltage level associated with the electrode while the electrical stimulation pulse is being applied by way of the electrode. FIG. 4 shows an exemplary voltage measuring circuit 400 that may be included in cochlear implant 108 and that may be used to measure the voltage level associated with an electrode 402 (which may be one of electrodes 112, for example) while the electrical stimulation pulse is being applied by way of the electrode 402. As shown in FIG. 4, voltage measuring circuit 400 may include a differential amplifier 404 ("AMP 404") and an analog-to-digital converter 406 ("ADC 406"). It will be recognized that the voltage measuring circuit components shown in FIG. 4 are merely representative of the many different components that may be included in voltage measuring circuit 400 and that voltage measuring circuit 400 may include additional or alternative components as may serve a particular implementation. FIG. 4 also shows a current source 408 that generates the electrical stimulation pulse that is applied by way of electrode 402 and a DC blocking capacitor 410.

As illustrated in FIG. 4, AMP 404 may have a first input electrically connected to a node A common with electrode 402 and a second input electrically connected to ground B. As shown, ADC 406 may be electrically coupled to an output of AMP 404. AMP 404 may detect the voltage level of electrode 402 and output an analog signal representative of an amplified version of the voltage level associated with electrode 402. ADC 406 may convert the analog signal to a digital value representative of the voltage level associated with electrode 402.

A signal amplitude of an electrical stimulation pulse at normal stimulation levels is typically large. In view of this, and because the signal-to-noise ratio of the electrical pulse is relatively high, voltage measuring circuit 400 may be implemented by relatively low gain and low power consuming components. For example, AMP 404 may have an approximate maximum gain of 20 dB. ADC 406 may also be implemented by a relatively low power component with a power consumption level suitable to digitize the analog signal output from AMP 404.

By way of example, stimulation management facility 302 may direct current source 408 to generate and apply an electrical stimulation pulse representative of an audio signal to electrode 402. Impedance management facility 304 may determine an impedance of electrode 402 by, for example, directing voltage measuring circuit 400 to measure a voltage between node A and ground B in FIG. 4 while the electrical stimulation pulse representative of the audio signal is being applied by way of electrode 402.

In some examples, an electrical stimulation pulse delivered to electrode 402 during a normal operation of the cochlear implant system 100 is a high current pulse having a high voltage. In these examples, the voltage level associated with electrode 402 may be measured without amplification, thereby obviating the need for AMP 404. Accordingly, in some implementations, a bypass circuit may be provided as part of a voltage measuring circuit included in cochlear implant 108.

Figure 5:
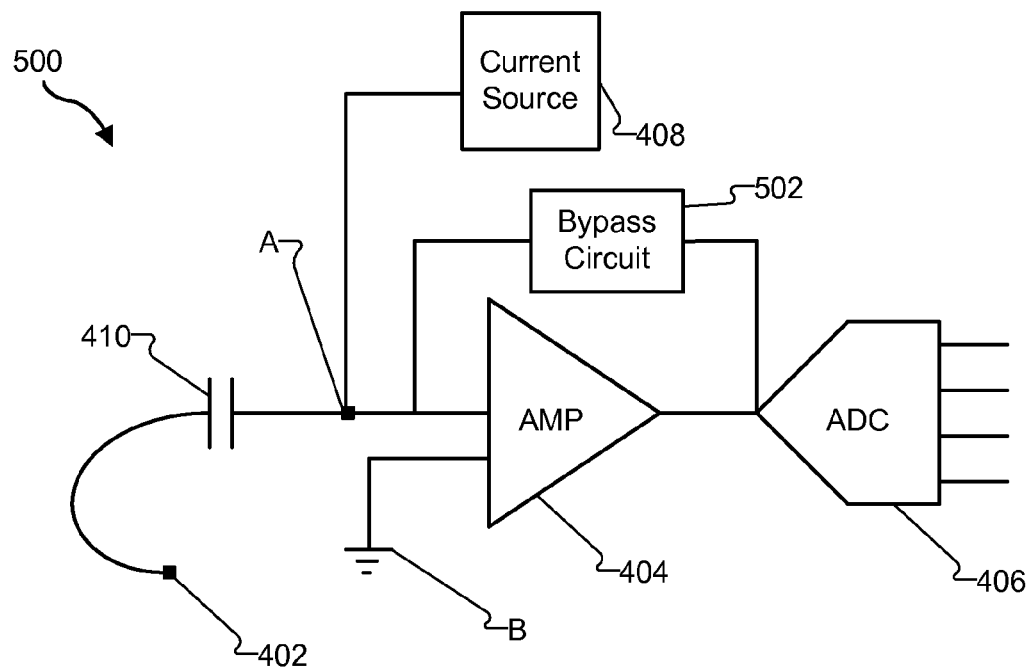
FIG. 5 illustrates another exemplary voltage measuring circuit according to principles described herein.

To illustrate, FIG. 5 shows an exemplary voltage measuring circuit 500, which is similar to voltage measuring circuit 400 except that in voltage measuring circuit 500, a bypass circuit 502 is provided and configured to selectively bypass AMP 404. The bypass circuit 502 may allow a signal representative of the voltage level of electrode 402 to be received by ADC 406 without being amplified by AMP 404. To this end, the impedance management facility 304 may direct cochlear implant 108 to bypass AMP 404 by way of bypass circuit 502 when an amplitude of the electrical stimulation pulse is above a predetermined threshold value. The predetermined threshold value may be a value at which ADC 406 is able to measure the voltage level associated with electrode 402 without the voltage level being amplified by AMP 404. For example, ADC 406 may be able to measure a voltage level of 1.0 mV without being amplified by AMP 404. In such a situation, impedance management facility 304 may use bypass circuit 502 to bypass AMP 404 when the voltage level is at or above 1.0 mV. Bypass circuit 502 may be implemented in any suitable manner as may suit a particular implementation. For example, bypass circuit 502 may be implemented by a switch and/or any suitable software component.

Returning to FIG. 3, impedance management facility 304 may measure the impedance of the electrode at different times to determine whether the impedance of electrode has changed over a period of time. To illustrate, a cochlear implant patient may be presented with an audio signal while, for example, watching a television program. Stimulation management facility 302 may receive the audio signal and direct cochlear implant 108 to generate and apply an electrical stimulation pulse representative of the audio signal by way of the electrode. Impedance management facility 304 may determine an impedance of the electrode by directing cochlear implant 108 to measure a voltage level associated with the electrode while the electrical stimulation pulse is being applied by way of the electrode. The voltage level may be measured, for example, through a voltage measuring circuit such voltage measuring circuits 400 or 500, as described above.

At any time subsequent to the electrical stimulation pulse being applied by way of the electrode (e.g., an hour subsequent to the stimulation pulse being applied by way of the electrode), stimulation management facility 302 may direct cochlear implant 108 to generate and apply an additional electrical stimulation pulse representative of the audio signal by way of the electrode. Impedance management facility 304 may determine an updated impedance of the electrode by directing cochlear implant 108 to measure an additional voltage level associated with the electrode while the additional electrical stimulation pulse is being applied by way of the electrode. Stimulation management facility 302 may determine a change in impedance that occurs during a time period between when the electrical stimulation pulse and the additional electrical stimulation pulse are applied by determining a difference between the updated impedance and the previously determined impedance.

In some examples, stimulation management facility 302 may be configured to adjust one or more stimulation parameters associated with the cochlear implant system 100 based on the determined difference between the updated impedance and the previously determined impedance of the electrode. To illustrate, in the example discussed above, stimulation management facility 302 may adjust one or more electrical stimulation parameters if the measured impedance of the electrode varies between the time when the patient is watching the television program and the time when the patient has the conversation with the family member. Multiple updated impedances of the electrode may be measured as described herein to continually adjust/optimize electrical stimulation parameters associated with the electrode on-the-fly. The electrical stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, ramp on time, and ramp off time of the stimulation current that is applied to the stimulation site. For example, if an increase in impedance for the electrode is detected, stimulation management facility 302 may be configured to adjust one or more stimulation parameters such that the total electric charge applied via the electrode remains constant. These changes may be made in real time and during the normal operation of the cochlear implant system 100 in order to attempt to maintain a consistent loudness level as perceived by the patient.

To illustrate, a stimulation pulse representing an audio signal may applied to the electrode. After processing the impedance detected by impedance management facility 304, stimulation management facility 302 may determine that the impedance of the electrode has doubled. This change in impedance may result in stimulation management facility 302 reducing the amplitude of the current to be applied to the electrode by one half for future electrical stimulation pulses to compensate for the change in impedance.

Additional or alternative stimulation parameters may be adjusted to compensate for a detected change in electrode impedance. For example, a most comfortable stimulation level ("M level") and/or a quiet sound level ("T level") corresponding to electrical stimulation applied to a patient may be adjusted in real time during the normal operation of the cochlear implant system 100 to compensate for a detected change in electrode impedance. Additionally or alternatively, values corresponding to a current amplitude versus pulse width curve may be stored in a look up table and used to determine an appropriate pulse width for a particular current amplitude caused by a change in impedance. These values may be obtained using any suitable heuristic and/or empirical data as may serve a particular application. Additionally or alternatively, if an increase in impedance for a particular the electrode is detected, stimulation management facility 302 may be configured to adjust one or more stimulation parameters such that the total electric charge of electrical stimulation current applied via the electrode remains constant. It will be recognized that additional or alternative stimulation parameters governing the electrical stimulation current applied via the electrode may be adjusted in response to a detected change in electrode impedance as may serve a particular application.

Figure 6:
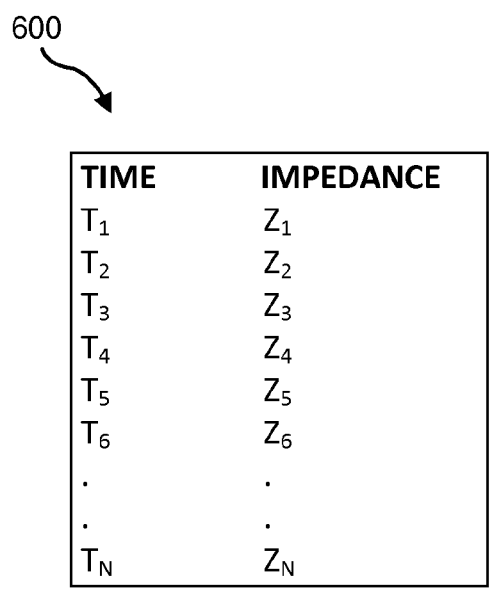
FIG. 6 illustrates an exemplary log of impedances according to principles described herein.

In some implementations, stimulation management facility 302 may be configured to maintain a log of impedances associated with the electrode. To illustrate, FIG. 6 shows an exemplary log of impedances 600 that may be maintained by stimulation management facility 302. As shown in FIG. 6, log of impedances 600 may include an impedance $Z_1$ determined at time $T_1$, an updated impedance $Z_2$ determined at time $T_2$ and so forth up to an updated impedance $Z_N$ determined at time $T_N$. The impedance of the electrode may be determined periodically at predetermined intervals or randomly at different times during a given time period (e.g., during a day, a week, a month, a year etc.). For example, impedance management facility 304 may determine an updated impedance of the electrode every two hours and stimulation management facility 302 may store each updated impedance through, for example, storage facility 306 as impedance data 310. Alternatively, impedance management facility 304 may determine an updated impedance of the electrode multiple times randomly during a 24 hour period. Alternatively, impedance management facility 304 may determine an updated impedance during a normal operation of the cochlear implant system when an audio signal of a predetermined amplitude is presented to the patient. For example, impedance management facility 304 may determine an updated impedance every time, or at select times, when a patient is presented with a sound above a certain volume. Log of impedances 600 may be used to adjust and/or optimize one or more of the stimulation parameters described herein. For example, stimulation management facility 302 may adjust one or more stimulation parameters each time an updated impedance is determined if it is determined that a change in impedance of the electrode has occurred. In addition, log of impedances 600 may be used for stimulation strategy development as well as for facilitating diagnostic and research work that may aid in developing cochlear implant systems with improved performance.

Figure 7:
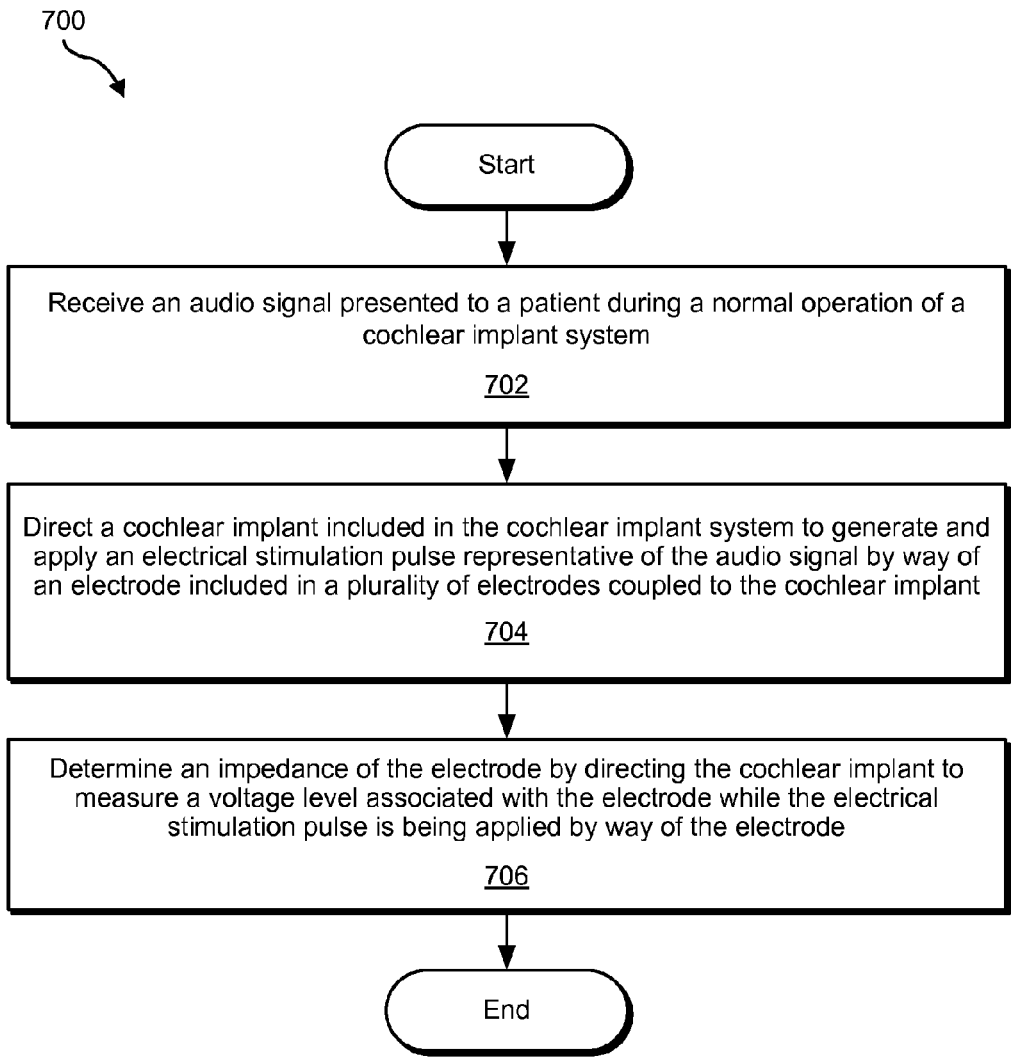
FIG. 7 illustrates an exemplary method of measuring impedance of a cochlear implant electrode according to principles described herein.

FIG. 7 illustrates an exemplary method 700 of measuring impedance of a cochlear implant electrode. While FIG. 7 illustrates exemplary steps according to one embodiment, other embodiments may omit, add to, reorder, and/or modify any of the steps shown in FIG. 7. One or more of the steps shown in FIG. 7 may be performed by sound processor 104 and/or any implementation thereof.

In step 702, a sound processor included in a cochlear implant system associated with a patient receives an audio signal presented to the patient during a normal operation of the cochlear implant system. Step 702 may be performed in any of the ways described herein.

In step 704, the sound processor directs a cochlear implant included in the cochlear implant system to generate and apply an electrical stimulation pulse representative of the audio signal by way of an electrode included in a plurality of electrodes coupled to the cochlear implant. Step 704 may be performed in any of the ways described herein.

In step 706, the sound processor determines an impedance of the electrode by directing the cochlear implant to measure a voltage level associated with the electrode while the electrical stimulation pulse is being applied by way of the electrode. Step 706 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system associated with a patient, the sound processor comprising:
   a stimulation management facility that
      receives an audio signal presented to the patient during a normal operation of the cochlear implant system, and
      directs a cochlear implant of the cochlear implant system to generate and apply an electrical stimulation pulse representative of the audio signal by way of an electrode included in a plurality of electrodes coupled to the cochlear implant; and
   an impedance management facility that determines an impedance of the electrode by directing the cochlear implant to measure a voltage level associated with the electrode while the electrical stimulation pulse that represents the audio signal presented to the patient during the normal operation of the cochlear implant system is being applied by way of the electrode.

2. The sound processor of claim 1, wherein the stimulation management facility adjusts one or more stimulation parameters associated with the cochlear implant system based on the determined impedance.

3. The sound processor of claim 2, wherein the one or more stimulation parameters comprise at least one of a pulse width, a total electric charge of electrical stimulation current, a most comfortable current level, and a quiet sound level.

4. The sound processor of claim 1, wherein:
   the stimulation management facility directs the cochlear implant to generate and apply an additional electrical stimulation pulse representative of the audio signal by way of the electrode subsequent to the application of the electrical stimulation pulse; and
   the impedance management facility determines an updated impedance of the electrode by directing the cochlear implant to measure an additional voltage level associated with the electrode while the additional electrical stimulation pulse is being applied by way of the electrode.

5. The sound processor of claim 4, wherein the stimulation management facility
   determines a change in impedance that occurs during a time period between when the electrical stimulation pulse and the additional electrical stimulation pulse are applied by determining a difference between the updated impedance and the impedance; and
   adjusts one or more stimulation parameters associated with the cochlear implant system based on the determined change in impedance.

6. The sound processor of claim 1, wherein the stimulation management facility maintains a log of impedances associated with the electrode; and includes the determined impedance in the log.

7. A system comprising:

a cochlear implant implanted within a patient and electrically coupled to a plurality of electrodes; and a sound processor communicatively coupled to the cochlear implant;

wherein the sound processor receives an audio signal presented to the patient during a normal operation of the cochlear implant, directs the cochlear implant to generate and apply an electrical stimulation pulse representative of the audio signal by way of an electrode included in the plurality of electrodes, and determines an impedance of the electrode by directing the cochlear implant to measure a voltage level associated with the electrode while the electrical stimulation pulse that represents the audio signal presented to the patient during the normal operation of the cochlear implant system is being applied by way of the electrode.

8. The system of claim 7, wherein the cochlear implant comprises a voltage measuring circuit that performs the measurement of the voltage level associated with the electrode, the voltage measuring circuit comprising:

a differential amplifier having a first input electrically connected to a node common with the electrode and a second input electrically connected to ground; and an analog-to-digital converter ("ADC") electrically coupled to an output of the differential amplifier;

wherein the differential amplifier outputs an analog signal representative of an amplified version of the voltage level associated with the electrode; and wherein the ADC converts the analog signal to a digital value representative of the voltage level associated with the electrode.

9. The system of claim 8, wherein:

the voltage measuring circuit further comprises a bypass circuit that allows a signal representative of the voltage level of the electrode to be received by the ADC without being amplified by the differential amplifier; and the sound processor directs the cochlear implant to bypass the differential amplifier by way of the bypass circuit when an amplitude of the electrical stimulation pulse is above a predetermined threshold value.

10. The system of claim 9, wherein the predetermined threshold value is a value at which the ADC can measure the voltage level associated with the electrode without the voltage level being amplified.

11. The system of claim 7, wherein the sound processor:

directs the cochlear implant to generate and apply an additional electrical stimulation pulse representative of the audio signal by way of the electrode subsequent to the application of the electrical stimulation pulse, and determines an updated impedance of the electrode by directing the cochlear implant to measure an additional voltage level associated with the electrode while the additional electrical stimulation pulse is being applied by way of the electrode.

12. The system of claim 11, wherein the sound processor:

determines a change in impedance that occurs during a time period between when the electrical stimulation pulse and the additional electrical stimulation pulse are applied by determining a difference between the updated impedance and the impedance, and adjusts one or more stimulation parameters associated with the cochlear implant system based on the determined change in impedance.

13. A method comprising:

receiving, by a sound processor included in a cochlear implant system associated with a patient, an audio signal presented to the patient during a normal operation of the cochlear implant system;

directing, by the sound processor, a cochlear implant included in the cochlear implant system to generate and apply an electrical stimulation pulse representative of the audio signal by way of an electrode included in a plurality of electrodes coupled to the cochlear implant; and determining, by the sound processor, an impedance of the electrode by directing the cochlear implant to measure a voltage level associated with the electrode while the electrical stimulation pulse that represents the audio signal presented to the patient during the normal operation of the cochlear implant system is being applied by way of the electrode.

14. The method of claim 13, further comprising:

bypassing, by the sound processor, a differential amplifier in a voltage measuring circuit that measures the voltage level associated with the electrode if an amplitude of the electrical stimulation pulse is above a predetermined threshold.

15. The method of claim 13, further comprising adjusting, by the sound processor, one or more stimulation parameters associated with the cochlear implant system based on the determined impedance.

16. The method of claim 15, wherein the one or more stimulation parameters comprise at least one of a pulse width, a total electric charge of electrical stimulation current, a most comfortable current level, and a quiet sound level.

17. The method of claim 13, further comprising:

directing, by the sound processor, the cochlear implant to generate and apply an additional electrical stimulation pulse representative of the audio signal by way of the electrode subsequent to the application of the electrical stimulation pulse; and determining, by the sound processor, an updated impedance of the electrode by directing the cochlear implant to measure an additional voltage level associated with the electrode while the additional electrical stimulation pulse is being applied by way of the electrode.

18. The method of claim 17, further comprising:

determining, by the sound processor, a change in impedance that occurs during a time period between when the electrical stimulation pulse and the additional electrical stimulation pulse are applied by determining a difference between the updated impedance and the impedance; and adjusting, by the sound processor, one or more stimulation parameters associated with the cochlear implant system based on the determined change in impedance.

19. The method of claim 17, wherein the determining of the updated impedance is performed while the audio signal is presented to the patient.

20. The method of claim 13, wherein the determining of the impedance is performed when an amplitude of the audio signal is above a predetermined amplitude.

* * * * *